US00PP23476P2

(12) United States Plant Patent
Carruth

(10) Patent No.: US PP23,476 P2
(45) Date of Patent: Mar. 19, 2013

(54) HYBRID TEA ROSE PLANT NAMED 'WEKMEREWBY'

(50) Latin Name: *Rosa hybrida*
Varietal Denomination: WEKmerewby

(75) Inventor: Thomas F. Carruth, Altadena, CA (US)

(73) Assignee: Weeks Wholesale Rose Grower, Inc., Pomona, CA (US)

( * ) Notice: Subject to any disclaimer, the term of this patent is extended or adjusted under 35 U.S.C. 154(b) by 12 days.

(21) Appl. No.: 13/317,186

(22) Filed: Oct. 12, 2011

(51) Int. Cl.
*A01H 5/00* (2006.01)

(52) U.S. Cl. ..... Plt./138; Plt./101; Plt./130

(58) Field of Classification Search ..... Plt./138, Plt./130, 101
See application file for complete search history.

*Primary Examiner* — Susan McCormick Ewoldt
(74) *Attorney, Agent, or Firm* — McKee, Voorhees & Sease, P.L.C.

(57) ABSTRACT

A new variety of Hybrid Tea rose suitable for garden decoration, having flowers of saturate rose pink coloration.

1 Drawing Sheet

Classification: The present invention relates to a new *Rosa hybrida* plant.

Variety denomination: The new plant has the varietal denomination 'WEKmerewby'.

BACKGROUND OF THE INVENTION

This invention relates to a new and distinct variety of Hybrid Tea Rose. It has as its seed parent the variety known as 'WEKmeredoc' (not patented) and as its pollen parent the variety known as 'WEKisosblip' (U.S. Plant Pat. No. 18,554).

SUMMARY OF THE INVENTION

Among the features which distinguish the new variety from other presently available and commercial rose cultivars known to the inventor are the following combinations of characteristics: its very strong damask to somewhat fruity fragrance, its upright tall growing habit and its abundant blooms on long cutting stems. The plant has an upright growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKmerewby' may be asexually propagated by cuttings, budding and grafting. The budding and grafting successfully occurred on the plant/rootstock *Rosa hybrida* cv. Dr. Huey (not patented).

COMPARISON WITH PARENTS

The new rose may be distinguished from its seed parent, 'WEKmeredoc' by the following combination of characteristics: whereas 'WEKmerewby' bears double flowers (about 26 to 38 petals) of saturate rose pink coloration, 'WEKmeredoc' bears double flowers of light pink coloration with significantly lesser petalage (about 17 to 25 petals). The new variety has an upright tall growing habit (about 170 to about 190 cm. in height), whereas the seed parent has an upright medium height significantly shorter growing habit (about 90 cm. in height).

The new variety may be distinguished from its pollen parent, 'WEKisosblip' by the following combination of characteristics: whereas 'WEKmerewby' bears large size flowers (about 11.0 to about 12.5 cm. in diameter) of saturate rose pink coloration, 'WEKisosblip' bears significantly smaller flowers (about 6.7 to about 10.0 cm. in diameter) of red-purple with a lavender eye coloration. The new variety has an upright tall growing habit (about 170 to about 190 cm. in height), whereas the pollen parent has an upright somewhat spreading medium height significantly shorter growing habit (about 110 to about 130 cm. in height).

COMPARISON WITH THE CLOSEST COMMERCIALLY AVAILABLE CULTIVAR

The new variety may be distinguished from its closest commercially available cultivar, Queen Elizabeth (not patented) by the following combination of characteristics: whereas 'WEKmerewby' bears double flowers (about 26 to 38 petals) of saturate rose pink coloration, Queen Elizabeth bears double flowers of significantly lighter pink coloration and heavier petalage (about 38 to 40 petals). The new variety has flowers with very strong damask to somewhat fruity fragrance, whereas the closest commercially available cultivar has flowers with less fragrance.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. in the month of August. Phenotypic expression may vary with environmental, cultural and climatic conditions, as well as differences in conditions of light and soil.

FLOWER

The new variety usually bears its flowers in clusters of two to four or more per stem. Flowers are borne in regular flat to rounded clusters on strong long stems (about 55 to about 65 cm.). Outdoors, the plant blooms very abundantly and nearly continuously during the growing season. The flowers have a very strong damask to somewhat fruity fragrance.

BUD

The peduncle is about 3.5 to about 4.2 cm. in length, of average caliper (about 0.2 to about 0.3 cm. in diameter), and usually erect but sometimes slightly bending. It is almost entirely smooth with some stipitate glands. Peduncle color is between 144A and 144B sometimes lightly suffused, especially on the side exposed to the sun, with near 184C.

Before the calyx breaks, the bud is about 1.6 to about 1.9 cm. in diameter at the widest point, about 2.0 to about 2.3 cm. in length, and pointed to ovoid in shape. The surface of the bud bears between 1 to 6 foliaceous appendages and few stipitate glands, usually with slender foliaceous parts extending beyond the tip of the bud about ¼ or more of its length. Bud color is between 144A and 144B.

The sepals are about 2.3 to about 2.6 cm. in length and about 0.7 to about 0.9 cm. in width at the widest point. The outer surface color of the sepal is between 144A and 144B. The inner surface color of the sepal is near 147C. The inner surface of the sepal is covered with fine wooly tomentum; sepal margins are lined with many stipitate glands.

The receptacle of the flower is of medium length (about 0.5 to about 0.7 cm.) and average in caliper (about 0.9 to about 1.1 cm. in diameter). The receptacle is urn-shaped in form. Its surface is very smooth with moderately thick fleshy walls. The receptacle color is between 144A and 144B.

As the petals open (after the calyx breaks), the bud is about 2.4 to about 2.6 cm. in diameter at the widest point, about 3.1 to about 3.3 cm. in length, and somewhat ovoid to globular in form. The color of the under and upper surfaces of the newly opened petals is between 58A and 63B. At the point where the petal attaches, there is a moderately large zone of between 11D and 155C.

BLOOM

When fully open, the bloom ranges from about 11 to about 12.5 cm. in diameter. Petalage is double with about 26 to 38 petals and about 3 to 7 petaloids irregularly arranged. When partially open, the bloom form is moderately cupped to globular, and the petals are somewhat cupped with petal edges slightly reflexed outward. When fully open, the bloom form is more cupped to full, and the petals are moderately cupped to somewhat undulated with petal edges moderately reflexed to somewhat rolled outward.

PETALS

The substance of the petals is somewhat heavy and of medium thickness, with upper surfaces somewhat velvety and under surfaces more satiny. The petals are about 4.8 to about 5.5 cm. in length and about 4.6 to about 5.4 cm. in width at the widest point. Petal margins are usually entire.

The outer petals are nearly round to broadly obovate in shape with moderately rounded apices that sometimes exhibit one to two notches.

The inner petals are more narrowly obovate in shape with apices somewhat rounded to flat that usually exhibit one to two notches.

Petaloids are about 2.6 to about 3.8 cm. in length and about 1.1 to about 1.4 cm. in width at the widest point. Petaloids are shaped somewhat irregular to narrowly obovate with somewhat rounded apices.

NEWLY OPENED FLOWER

The under surface color of the outer, intermediate and inner petals is between 61C and 66C. The upper surface color of the outer, intermediate and inner petals is between 67B and 67C. At the point where the petal attaches on the under and upper surfaces, there is a moderately large zone of near 155A.

The under and upper surface colors of the petaloids are similar in coloration to the upper and under surfaces of the outer, intermediate and inner petals.

The general tonality of the newly opened flower is between 67B and 67C.

THREE-DAY-OLD FLOWER

The under surface color of the outer, intermediate and inner petals is near 67C. The upper surface color of the outer, intermediate and inner petals is between 67C and 68A. At the point where the petal attaches on the under and upper surfaces, there is a moderately large zone of near 155B.

The under and upper surface colors of the petaloids are similar in coloration to the upper and under surfaces of the outer, intermediate and inner petals.

The general tonality of the three-day-old flower is between 67C and 68A.

On the spent bloom, the petals usually drop off cleanly and are not particularly affected by cold, hot or dry weather.

In August in Pomona, Calif., blooms on the bush growing outdoors generally last about four to five days. Cut roses from plants grown outdoors and kept at normal indoor living temperatures generally last about four to five days.

MALE REPRODUCTIVE ORGANS

Stamens are average to many in number (average about 120) and are arranged regularly about the pistils. The filaments are of somewhat irregular length (about 1.2 to about 1.6 cm.) most with anthers. Filaments are near 11C in color. The anthers are of medium size for the class and all open approximately at the same time. Anther color when immature is near 12B on the external part and near 11B on the internal part. Anther color at maturity is near 12D on the external part and near 165A on the internal part. Pollen is moderate to abundant and near 11D in color.

FEMALE REPRODUCTIVE ORGANS

Pistils vary in number (average about 80). The styles are moderately uneven, somewhat short to average in length (about 0.4 to about 0.6 cm.), moderately thin in caliper, and mostly bunched. Stigma color is near 4C. Style color is near 4D usually heavily suffused with near 45D especially on the upper two thirds. Ovaries are usually all enclosed in the calyx.

Hips are average in length (about 2.4 to about 3.0 cm.), somewhat globular in form, and near 30C in color when ripe.

The hip surface is very smooth with moderately thick fleshy walls. The sepals are mostly permanent, short to medium in length, and somewhat recurved in shape.

The seeds are irregularly rounded, smooth in texture, approximately 12 to about 18 per hip, about 0.4 to about 0.7 cm. in diameter at the widest point and near 165D in color.

FOLIAGE

The compound leaves are usually comprised of three to five leaflets and are borne very abundantly. The five-leaflet leaves are about 9.6 to about 13.5 cm. in length and about 8.7 to about 12.2 cm. in width at the widest point, somewhat heavy to leathery in texture, and somewhat matte to semi-glossy in finish on the upper side and matte in finish on the under side. The terminal leaflets are about 4.7 to about 7.8 cm. in length and about 3.4 to about 4.8 cm. in width at the widest point, shaped broadly oval to somewhat ovate with very acute apices and somewhat round to slightly acute bases. Their margins are usually simply serrate.

The upper surface color of the mature leaf is between 137A and 147A. The under surface color of the mature leaf is between 137C and 147B. The upper surface color of the young leaf is near 144B, often moderately suffused with between 183C and 185B. The under surface color of the young leaf is near 144B, usually heavily suffused with between 183C and 187C.

The rachis is average to heavy in caliper and moderately smooth. The upper side is somewhat shallowly grooved with a few stipitate glands on the edges of the grooves. The under side of the rachis is moderately smooth with few stipitate glands and sometimes with one to two small prickles. The rachis color is near 144A on the under and upper side.

The stipules are about 1.4 to about 1.7 cm. in length and somewhat narrow in width (about 0.7 to about 0.8 cm.) with moderately short to medium length straight points that usually turn out at an angle of more than 45 degrees. The under and upper surface color of the stipule is near 144A.

The petiole is average in caliper and very smooth. The upper side is moderately shallowly grooved with few stipitate glands on the edges of the grooves. The under side of the petiole is very smooth with few stipitate glands. The petiole is about 0.2 to about 0.3 cm. in length and about 0.15 to about 0.2 cm in width at the widest point. The petiole color is near 144A on the under and upper sides.

The plant displays an above average degree of resistance to powdery mildew and rust as compared to other commercial varieties grown under comparable conditions in Pomona, Calif. The plant's winter hardiness and drought/heat tolerance are yet to be determined.

GROWTH

The plant has an upright tall growing habit (about 170 to about 190 cm. in height and about 90 to about 110 cm. spread at the widest point), with very full branching. It displays very vigorous growth and the canes are of medium to heavy caliper for the class (about 1.8 to about 2.4 cm. in diameter at the widest point).

The color of the major stems is near 146C. They bear many large prickles that are about 0.9 to about 1.2 cm. in length. The large prickles are almost straight to angled moderately downward with a medium length somewhat broad base; prickle color is between 166B and 165A. The major stem bears few small prickles of similar shape and coloration.

The color of the branches is between 144A and 146A. They bear some large prickles which are of similar size and shape to the large prickles on the major stems; prickle color is between 160C and 162D. The branches bear few small prickles of similar shape and coloration.

The color of the new shoots is near 144B often moderately suffused with between 183C and 187C. They bear some large prickles which are of similar size and shape to the large prickles on the major stems; prickle color is near 160C often moderately suffused with between 185C and 183C. The shoots bear some small prickles of similar shape and coloration.

I claim:

1. A new and distinct Hybrid Tea rose plant of the variety substantially as described and illustrated herein.

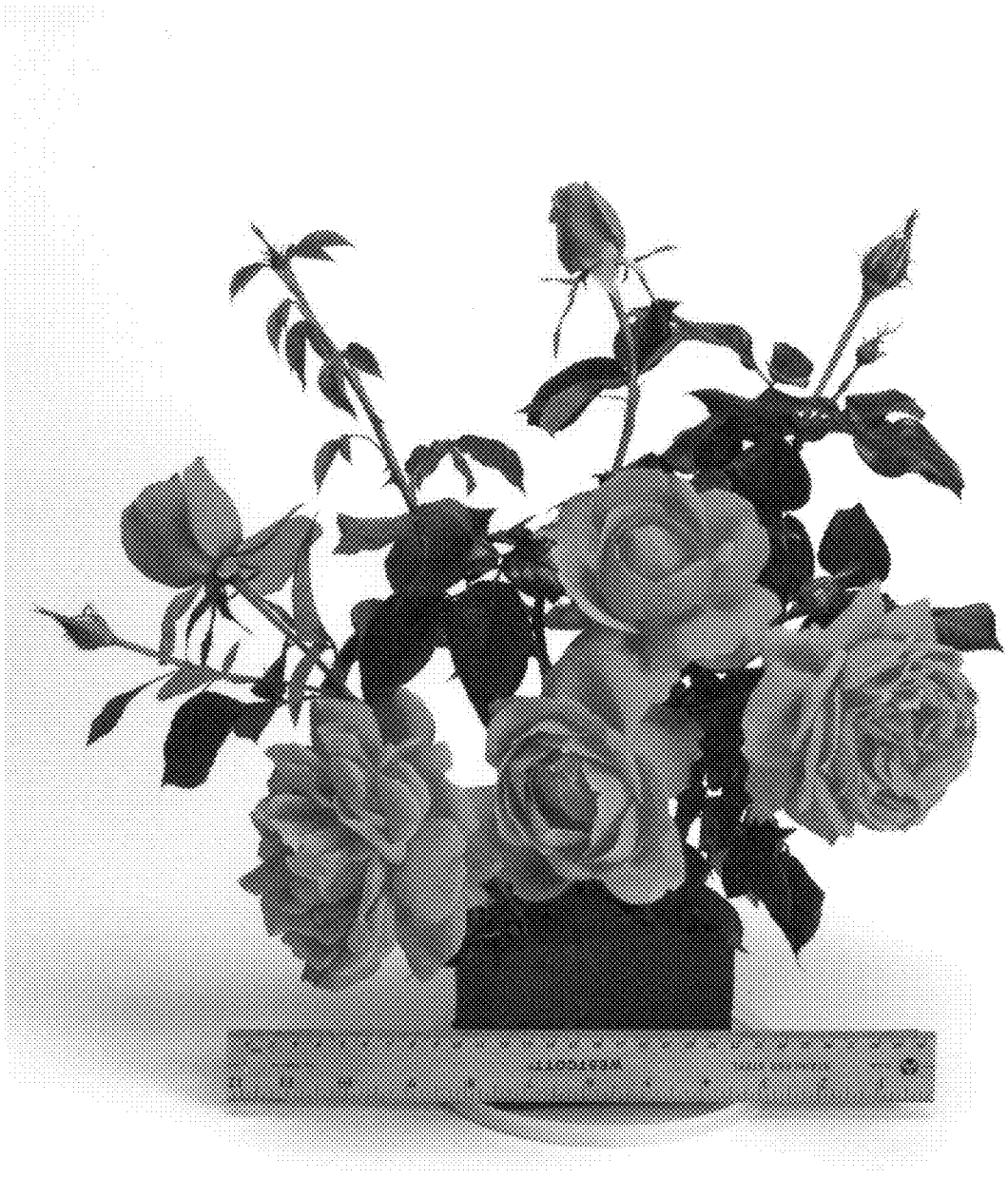

* * * * *